United States Patent [19]

Hoshino et al.

[11] Patent Number: 4,543,259

[45] Date of Patent: Sep. 24, 1985

[54] SUBSTANCE TH69E AND IMMUNOPOTENTIATOR CONTAINING THE SAME

[75] Inventors: Fumihiko Hoshino; Takahiro Yamaguchi; Nobuyuki Abe, all of Sendai; Nobuyuki Watabe, Izumi; Yoshiteru Katzukura; Tadahiko Hoshino, both of Sendai; Yoko Utsumi, Izumi; Yoko Kuroda, Sendai, all of Japan

[73] Assignee: Teru Hoshino, Sendai, Japan

[21] Appl. No.: 352,068

[22] Filed: Feb. 24, 1982

Related U.S. Application Data

[63] Continuation-in-part of Ser. No. 162,201, Jun. 23, 1980, abandoned.

[30] Foreign Application Priority Data

Oct. 25, 1979 [JP] Japan .................................. 54-138190

[51] Int. Cl.$^4$ .......................... A61K 35/74; C12P 1/04
[52] U.S. Cl. ..................................... 424/116; 435/170
[58] Field of Search .......................... 424/116; 435/170

[56] References Cited

PUBLICATIONS

Nippon Acta Radiologica, 40, No. 5, 507, (1980).
Acta Histochem. Cytochem., 1979, Part I, 591.
Nippon Acta Radiologica, 40, Supplement, 89, (1980).
Japanese Journal of Bacteriology, 35, No. 1, 306, (1980).
Japanese Journal of Bacteriology, 35, No. 6, 779, (1980).
Proceedings of the Japanese Cancer Association, 40th Annual Meeting, 106, (1981).
Proceedings of the Society of Japanese Virologists, 29th Annual Meeting, 1082, (1981).

Primary Examiner—Jerome D. Goldberg
Attorney, Agent, or Firm—Oblon, Fisher, Spivak, McClelland & Maier

[57] ABSTRACT

A substance TH69E having the following characteristics: (a) elementary analysis: C: 24.25%, H: 4.46% and N: 6.55%; (b) molecular weight: about 60,000±15,000 (Biogel P-Series Column); (c) color: white amorphous powder; (d) decomposition point: 180° C. (as determined by a capillary method with use of Silicone Oil WF-30—the color changes to brown); (e) ultraviolet absorption spectrum: as shown in FIG. 1 of the drawings; (f) infrared absorption spectrum: as shown in FIG. 2 of the drawings; (g) pH: 6.7 to 7.1 in an aqueous solution; (h) solubility: soluble in water, and insoluble in ethanol, acetone, n-hexane, n-butanol and phenol; and (i) color reactions: phenol-sulfuric acid reaction, anthrone reaction, Molisch reaction, orcinol-hydrochloric acid reaction, Ninhydrin reaction being positive, and Elson-Morgan's reaction being negative. The substance TH69E exhibits immunopotentiating activities such as a collagen decomposition enhancing effect, an infection preventive effect and an interferon inducing effect.

6 Claims, 5 Drawing Figures

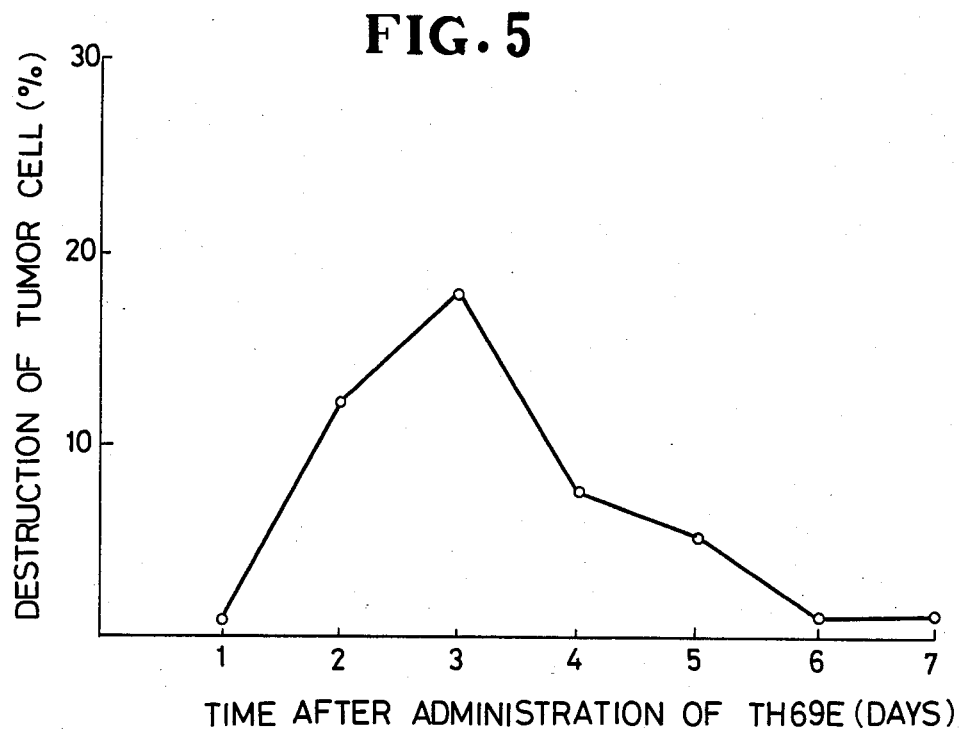

SUBSTANCE TH69E AND IMMUNOPOTENTIATOR CONTAINING THE SAME

CROSS-REFERENCE TO RELATED APPLICATIONS

This application is a continuation-in-part application of U.S. Pat. Ser. No. 162,201 filed June 23, 1980 now abandoned.

BACKGROUND OF THE INVENTION

1. Field of the Invention

This invention relates to a novel substance TH69E and an immunopotentiator containing such substance. More particularly, the invention is concerned with a substance TH69E which is obtainable from Streptococcus faecalis And. & Hord. TH-001 and which has a collagen decomposition enhancing effect, an infection preventing effect and an interferon inducing effect.

2. Description of the Prior Art

As is generally known, many of fibrous diseases are chronic in nature and hence are difficult to treat or cure with satisfactory results. The only conventional route to the treatment of these diseases is to administer a fibrosis decomposing enzyme by direct injection to any parts so affected. However, this existing technique is not necessarily ideal and satisfactory. A strong desire therefore prevails for the development of a therapeutic substance which is capable of curing such chronic diseases and which is also effectively useful as an immunopotentiator for infection prevention and interferon induction.

SUMMARY OF THE INVENTION

It is an object of the present invention to provide a novel substance TH69E.

Another object of the invention is to provide an immunopotentiator such as a fibrosis therapeutic composition, an infectious disease preventing composition and an interferon inducing agent.

Briefly, these objects and other objects of the invention as hereinafter will become more readily apparent can be attained by providing a substance TH69E which is derived from *Streptococcus faecalis* And. & Hord. TH-001, and an immunopotentiator containing the substance.

By the term immunopotentiator used herein is meant an agent which can exhibit substantially increased potency of the immune system.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 5 shows the relationship between the time course after the injection of TH69E and the effect of the peritoneal macrophage to lyse tumor cells.

DETAILED DESCRIPTION OF THE PREFERRED EMBODIMENTS

Figure 1:
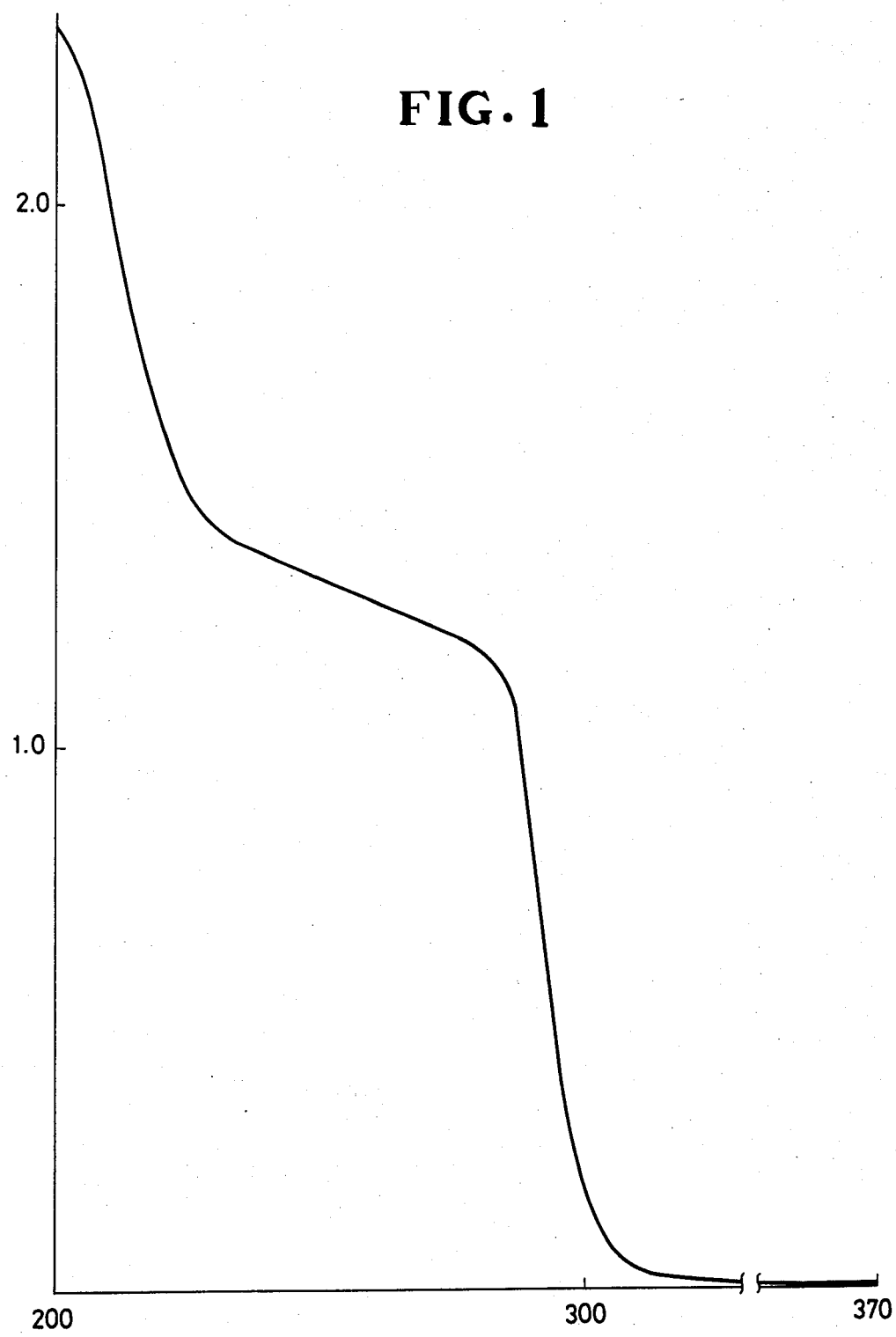
FIG. 1 shows the ultraviolet absorption spectrum of a substance TH69E according to the invention.

A substance TH69E of the present invention is prepared as will be advanced hereinafter.

A bacterium employed in the invention has the following bacteriological characteristics.

A. Morphological characteristics
  morphology: Streptococcus
  size 0.5 to 1.2 $\mu$
  motility: none
  gram stain: positive B. Growth in various culture media
  (1) meat juice agar plate culture: positive
  (2) meat juice agar slant culture: positive
  (3) meat broth culture: positive
  (4) meat broth culture containing 6.5% of sodium chloride: positive
  (5) litmus milk: reduction occurring
  (6) SF culture medium: positive C. Physiological characteristics
  (1) reduction of nitrates: negative
  (2) denitrification reaction: negative
  (3) hydrolysis of starch: negative
  (4) utilization of citric acid: negative
  (5) utilization of nitrates: negative
  (6) solubility in dyestuff: negative
  (7) urease: negative
  (8) oxidase: negative
  (9) catalase: negative
  (10) formation of hydrogen sulfide: negative
  (11) MR test: negative
  (12) VP test: positive
  (13) formation of indole: negative
  (14) growth range: 4.5 to 9.6 in pH and 10 to 45° C. in temperature
  (15) character against oxygen: facultative anaerobe
  (16) O-F test: F
  (17) liquefaction of gelatine: negative
  (18) hemolytic characteristics:
    horse blood agar ($\gamma$) and
    sheep blood agar ($\gamma$)
  (19) heat resistance at 60° C. for 30 minutes: positive D. Formation of an acid or gas from saccharides
  L-arabinose (negative), D-glucose (positive),
  D-fructose (positive), D-galactose (positive),
  D-mannose (positive), trehalose (positive),
  D-sorbitol (negative), D-mannitol (negative),
  fructose (positive), lactose (positive),
  melibiose (negative), cellobiose (positive),
  sucrose (positive), salicin (positive),
  maltose (positive) and Aesculin (positive)

From Bergey's Manual of Determinative Bacteriology, 8th Edition, it should be noted that the above characteristics correspond to those of *Streptococcus faecalis*. Accordingly, the present inventors have named the bacterium of the invention as *Streptococcus faecalis* And. & Hord. TH-001 and have deposited it with the Fermentation Research Institute of the Agency of Industrial Technology under FERM 4861 and the American Type Culture Collection under ATCC 31663.

A culture medium commonly used for bacteria belonging to genus Streptococcus may be utilized for culturing the bacterium of the invention. For example, a carbon source such as glucose or starch, a nitrogen source such as peptone or a yeast extract, and a minimal amount of a component such as an inorganic salt are appropriately selected for actual use. Particularly preferable is a culture medium comprising 10.0 g/l of glucose, 8.0 g/l of peptone, 4.0 g/l of a yeast powder, 3.0 g/l of sodium chloride and 2.5 g/l of sodium bicarbonate, which medium facilitates the growth of the bacterium and gives a good yield. Cultivation is preferably effected anaerobically at a temperature of about 37° C. for 24 to 48 hours.

The culture thus obtained is subjected to centrifugal separation whereby the intended bacterium is separated. The bacterium is boiled with hot water, and a water-saturated phenol in substantially the same amount is added to a solution extracted from the bacterium. The mixture is shaken vigorously under low temperature conditions, and the water layer is then separated for example by centrifugal separation. The treatment with a water-saturated phenol is repeated two more times. Ethyl ether is added to the resulting water layer, and the mixture is shaken. Thereafter, the water layer is separated to which is added ethanol in an amount of four times as much, thereby obtaining a precipitate. The precipitate is freeze dried to yield a white powder of the substance TH69E.

The TH69E substance thus obtained has the following physical and physiological activities.

A. Physical and Chemical Characteristics (1) elemental analysis: C:24.25%, H:4.46% and N:6.55%

(2) molecular weight: about 60,000±15,000 (Biogel P-Series Column)

(3) color: white amorphous powder (4) decomposition point: 180° C. (as determined by a capillary method with use of Silicone Oil WF-30, and the color changes to brown)

(5) ultraviolet absorption spectrum: as shown in FIG. 1

Figure 2:
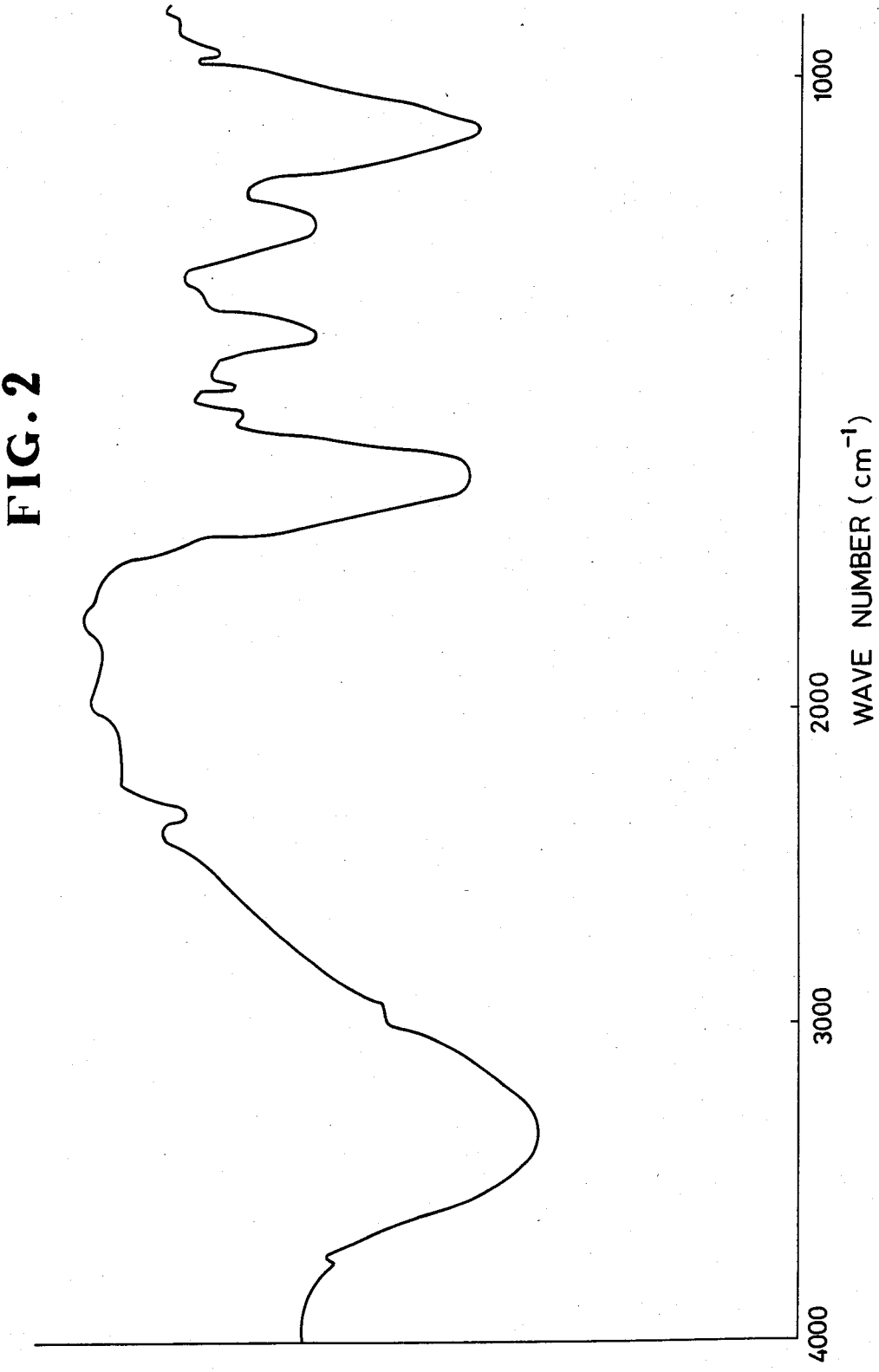
FIG. 2 shows the infrared absorption spectrum of TH69E.
Figure 3:
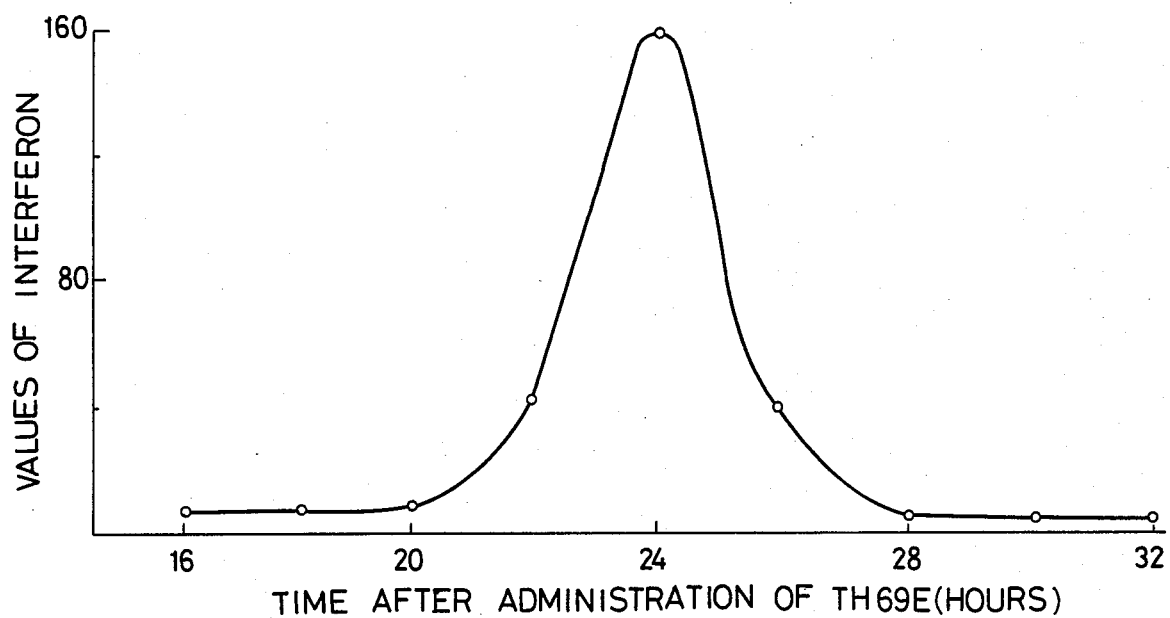
FIG. 3 shows the relationship between the time course after the injection of TH69E and the amounts of interferon induced.
Figure 4:
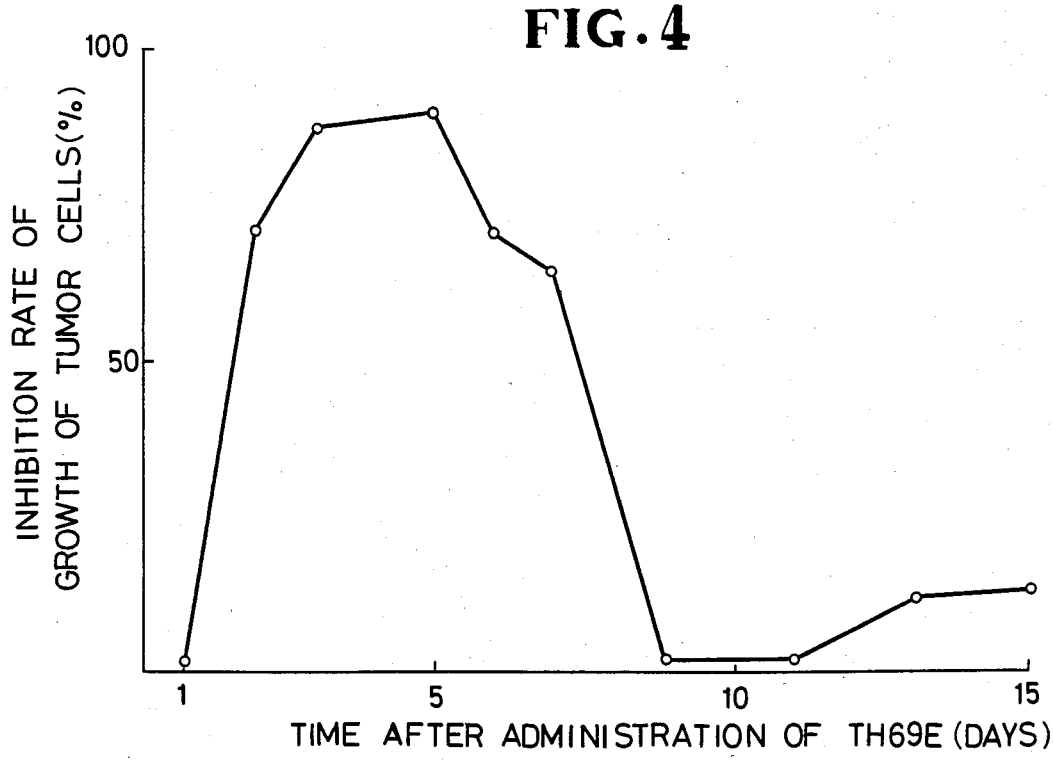
FIG. 4 shows the relationship between the time course after the injection of TH69E and the effect of the peritoneal macrophage to inhibit the growth of tumor cells.

(6) infrared absorption spectrum: as shown in FIG. 2

(7) pH: 6.7 to 7.1 in an aqueous solution (8) solubility: soluble in water, and insoluble in ethanol, acetone, n-hexane, n-butanol and phenol (9) color reactions: phenol sulfuric acid reaction, anthrone reaction, Molisch reaction and orcinol-hydrochloric acid reaction, Ninhydrin reaction being positive, and Elson-Morgan's reaction negative B. Biological Activity (determined by the following experiments)

(1) Collagen Decomposition Enhancing Effect

Experiment 1

TH69E was intraperitoneally injected to DDI mice, each group consisting of 10 animals having an average weight of 24 g, in a dose of 15 mg per kg of the weight of the mice at three intervals, namely, once (72 hours prior to killing), twice (72 and 48 hours prior to killing) and three times (72, 48 and 24 hours prior to killing). The resulting intraperitoneal cells were each collected and cultivated in a plastic culture dish for 2 hours. Any non-adherent cells were discarded, and the remaining cells were washed a few times. The plastic adherent cells were taken as the peritoneal macrophages of the mice. In this manner, the macrophages were prepared at a concentration of about $3 \times 10^7$ cells per culture dish. To each macrophage sample was added a Dulbecco medium containing 15% of a calf serum, and the mixture was cultivated in a $CO_2$ incubator for 24 hours. Subsequently, the Dulbecco medium was discarded, and the remainder was washed a few times with the same medium and cultivated in 10 ml of a serum-free Dulbecco medium in a $CO_2$ incubator for 72 hours. The cultured supernate and macrophage were separated, and the cell-free supernate was freeze dried. The macrophage was treated with trypsin, collected and homogenized with 10 ml of the Dulbecco medium, a supernate of which was freeze dried.

The cell-free supernate and the macrophage supernate were dissolved in 1 ml of distilled water, and 300 μl of each supernate was used for collagenase analysis.

The collagenase activity was determined pursuant to the method of McCroskery et al [Science, 182, 70 (1973)] by measuring the viscosity at the time collagen was decomposed by the action of the collagenase into gelatine. The reaction was carried out at 37° C. for 20 minutes with use of a reaction solution of McCroskery et al (final concentration: 50 mM of alginine, 600 g of collagen, 10 mM of calcium chloride, 100 mM of a tris-hydrochloric acid buffer solution of pH 7.6 and 200 mM of sodium chloride).

The results are shown in Table 1.

The results are expressed by the inverse values relative to the measured values of the viscosities reduced by the action of the collagenase of the peritoneal macrophage treated with TH69E, as compared to a control.

TABLE 1

| Peritoneal macrophage ($3 \times 10^7$) | Collagenase activity (1/measured values) | |
|---|---|---|
| TH69E administered (three times) | Macrophage supernate | 1.09 |
| | Cell-free supernate | 1.62 |
| TH69E administered (twice) | Macrophage supernate | 1.06 |
| | Cell-free supernate | 1.56 |
| TH69E administered (once) | Macrophage supernate | 1.18 |
| | Cell-free supernate | 1.68 |
| TH69E (not administered) | Macrophage supernate | 1.20 |
| | Cell-free supernate | 1.12 |

Experiment 2 (Effectiveness of TH69E on hemangioma)

Clinical studies were conducted to investigate the effectiveness of TH69E on hemangioma which was a benign tumor with expansion and elevated growth of blood vessels as well as connective tissue growth. Many fibroplasts were found in connective tissues, and fibrous changes through hyperfibroplasia were recognized. In these studies, several types of hemangioma were investigated since they were easily visible. Selected were twelve patients of 2 months to 4 years of age who had suffered from comparatively severe hemangioma. Amongst the patients, five cases were continuously administered with TH69E, and seven cases with a bacterium containing 1.2% TH69E, which bacterium was obtained in Example 1 as described hereinafter. The effectiveness was adjudged visually by the degrees of size reduction and color disappearance of the affected parts.

It was found that both the TH69E substance and the bacterium containing TH69E were effective for diseases having fibrous changes through fibroplasia.

The results are shown in Table 2.

As is clear from the results, collagenase is discharged from the macrophase due to the pretreatment of TH69E. In view of the fact that collagenase is known to decompose collagen which causes tissue fibrosis, the substance of the invention is considered to be effective as a fibrosis therapeutic agent.

In the tabulated results, the dose numerals parenthesized indicate the amounts of TH69E as having been administered in bacterium-receptive form. The grading notations of effectiveness are as follows:

+++: perfect (completely curable)
++: excellent
+: fair
−: cureless (inapplicable in these clinical studies)

with its peak at the time of about 24 hours after the intraperitoneal injection of TH69E. Experiment 4

TH69E was intraperitoneally injected to DDI male mice, each group consisting of 5 mice having an average weight of 24 g, in a dose of 150, 15 and 1.5 mg/kg of the weight of the mice. In the same manner as in Experiment 3, the reference mouce interferon was assayed with respect to the serums obtained 24 hours later.

The results are shown in Table 3.

TABLE 2

| No. | Patient | Sex | Age | Hemangioma region | Size (cm) | Dose (mg/day) | Administration term (year) | Observation | Effectiveness |
|---|---|---|---|---|---|---|---|---|---|
| 1 | M. M. | ♀ | 3 years | face | 3.0 × 2.5 | 50 | 1 | Blood vessel expansion completely disappeared and subcutaneous induration reducing | ++ |
| 2 | T. K. | ♀ | 12 months | face | 6.0 × 8.0 | 50 | 3 | Blood vessel expansion remaining very slightly | +++ |
| 3 | S. Y. | ♀ | 4 years | head | 2.5 × 2.3 | 100 | 3 | Blood vessel expansion disappeared but some subcutaneous induration still remaining | ++ |
| 4 | T. S. | ♀ | 3 months | right breast | 5.0 × 6.0 | 200 | 3 | Blood vessel expansion almost wholly disappeared but subcutaneous induration still remaining | ++ |
| 5 | K. N. | ♂ | 5 months | right chest | 10.0 × 10.0 | 200 | 3 | Completely disappeared | +++ |
| 6 | H. T. | ♀ | 3 months | left face | 10.0 × 10.0 | (50) | 4 | Blood vessel expansion disappeared but subcutaneous induration still remaining | ++ |
| 7 | S. S. | ♂ | 2 months | left shoulder and arm | 2.0 × 3.0 | (25) | 2 | Blood vessel expansion and subcutaneous induration disappeared | +++ |
| 8 | M. M. | ♀ | 2 months | right face | 4.0 × 4.0 | (25) | 2 | Completely disappeared | +++ |
| 9 | K. S. | ♀ | 3 months | left forearm | 12.0 × 6.0 | (37.5) | 2 | Blood vessel expansion still remaining slightly | + |
| 10 | K. S. | ♀ | 1 year | right lower leg | whole | (50) | 3 | Kippel-Weber syndrome disappearing very slowly | + |
| 11 | I. T. | ♂ | 2 years | face | 2.6 × 2.0 | (12.5) | 3 | Blood vessel expansion completely disappeared and subcutaneous induration reducing | ++ |
| 12 | K. M. | ♀ | 2 months | forechest | 6.0 × 8.0 | (37.5) | 3 | Kasbach-Meritis syndrome and blood vessel expansion completely disappeared | +++ |

(2) Interferon Inducing Effect
Experiment 3

TH69E was injected to DDI mice having an average weight of 24 g in a dose of 15 mg/kg of the weight of the mice, and the activity of interferon (a virus inhibiting substance) induced in the animal blood serums were determined.

The blood serums were obtained by killing 4 mice selected optionally from 50 mice at intervals of 4, 8, 12, 16, 20, 24, 28, 32, 36 and 42 hours after the injection of TH69E. Each of the serums was collected from the blood by centrifugal separation at 3,000 rpm for 10 minutes. Interferon was assayed on mouse L-929 cells in microplates by means of a plaque reduction method. The L-929 cells were seeded in the microplates with seriol dilutions of the serum containing IFN and incubated overnight at 37° C. Followed by removal of the serum, the cells were challenged with vesicular stomatitis virus and overlayed with 0.5% methyl cellulose. Approximately 24 hours later, the cells were each stained with a 1% solution of crystal violet, and the number of plaques per well was counted. The serum dilution required to reduce the number of plaques per well by 50% as compared to the virus control was finally converted to the international unit using a reference mouse interferon supplied by the U. S. National Institute of Health (NIH). This interferon was induced

TABLE 3

| Dose of TH69E | Titer (international unit) of interferon induced per ml of serum |
|---|---|
| 150 mg/kg | 40 |
| 15 mg/kg | 160 |
| 1.5 mg/kg | 30 |
| Saline | <4 |

Experiment 5

In order to characterize interferon induced by the intraperitoneal injection of TH69E to DDI mice in a dose of 15 mg/kg of the weight of the mice, test samples were treated, a first sample being at a temperature of 56° C. for one hour, a second one being with a glycine-hydrochloric acid buffer solution of pH 2.0 at a temperature of 4° C. for 18 hours, and a third one being with trypsin of the final concentration of 1,000 mcg/ml at a temperature of 37° C. for 3 hours. The titer of the remaining interferon was measured in the same manner as in Experiment 3.

The results are shown in Table 4.

TABLE 4

| Treatment | Interferon titer of TH69E per ml | Ratio of remaining values (%) |
|---|---|---|
| Heated at 56° C. | <20 | <16.7 |

TABLE 4-continued

| Treatment | Interferon titer of TH69E per ml | Ratio of remaining values (%) |
|---|---|---|
| for 1 hour | | |
| Kept at pH 2.0 at 4° C. for 18 hours | <20 | <16.7 |
| Treated with trypsin at 37° C. for 3 hours | <20 | <16.7 |
| Not treated | 120 | 100 |

These results indicate that the interferon induced by TH69E in the mouce serums loses its effect when treated with trypsin and that it is labile when treated with heat at 56° C. for one hour and with an acid at pH 2.0. Accordingly, the substance corresponds to an immune interferon reported by Falcoff and Wheelock [Falcoff, R., Some Properties of Virus and Immune Induced Human Lymphocyte Interferons, J. Glu. Virol 16, 251, (1972; and Wheelock, E. F., Interferon Like Virus Inhibitor Induced in Human Leukocytes by Histohemagglutinin, Science, 149, 310, (1965)].

It is apparent from the above results that interferon is induced by the intraperitoneal administration of TH69E in a dose of 1.5 to 150 mg/kg of the weight, preferably 10 to 50 mg/kg of the weight.

(3) Infection Preventive Effect

Experiment 5

DDI mice having an average weight of 20 g (6 weeks old) were infected with Listeria monocytogenes separated from a cerebrospinalic liquor of a patient of Listeriosis Meningitis, and the ratios of survival were determined with and without the injection of the substance of the present invention.

TH69E was intraperitoneally injected in a dose of 150, 15 and 1.5 mg/kg of the weight of the mice at the time of 72, 48 and 24 hours before the infection of Listeria monocytogenes. Control mice were injected with 0.5 ml of a saline.

Listeria monocytogenes was suspended in a saline to form a suspension containing $10^8$ cells/ml of Listeria monocytogenes, and 0.1 ml of the suspension was intravenously injected to each mouse from its tail, thereby infecting the mouse with Listeria monocytogenes. The observation was carried out for 30 days, and the mortality due to the infection was counted. The mice survived for 30 days were taken as permanently survived.

The results are shown in Table 5.

TABLE 5

| Dose of TH69E | Number of mice | Survivor after 30 days | Ratio of survivors (%) |
|---|---|---|---|
| 150 mg/kg | 16 | 7 | 43.8 |
| 15 mg/kg | 16 | 12 | 75.0 |
| 1.5 mg/kg | 16 | 10 | 62.5 |
| Saline (control) | 20 | 2 | 10.0 |

It is apparent from the above results that TH69E shows a preventive effect against Listeria monocytogenes infection at a concentration of 1.5 to 150 mg/kg of the weight. Further, similar infection preventive effects were obtained with respect to *Pseudomonas aeruginosa* and Eumycetes infection.

C. Acute Toxicity (LD$_{50}$)

| | Intraperitoneal administration (mg/kg of animal weight) | Oral administration (mg/kg of animal weight) | Intravenous administration (mg/kg of animal weight) |
|---|---|---|---|
| Mice | At least 1,200 | At least 2,800 | 375 |
| Rats | At least 1,200 | At least 2,000 | — |
| Guinea pigs | At least 1,200 | At least 2,000 | — |

The substance TH69E of the present invention may be administered in the form of an oral composition such as a powder, a granule, a tablet or a capsule, an oil base composition or an emulsion, an injection, or a suppository. Eligible doses of TH69E may be varied depending upon the purpose and the symptom of a particular case but may normally be 200 to 2,000 mg for an adult, which should preferably be administered 1 to 4 times a day.

Having generally described this invention, a further understanding can be obtained by reference to certain specific examples which are provided for purposes of illustration only and are not intended to be limiting unless otherwise specified.

EXAMPLE 1

*Streptcoccus faecalis* [Fermentation Research Institute, Acceptance No. FERM 4861 (ATCC 31663)] was cultivated on a liquid culture medium consisting of glucose (10.0 g/l), yeast (4.0 g/l), sodium chloride (3.0 g/l) and sodium bicarbonate (2.5 g/l) at 37° C. anaerobically for 48 hours. The cultivated mixture was subjected to centrifugal separation whereby the intended bacterium was obtained in an amount of 2.5 g per 1 of the culture medium.

100 g of the bacterium obtained above was dissolved in 300 ml of distilled water, and the mixture was boiled at 100° C. for 2 hours and then separated into a supernatant and a precipitate. A water-saturated phenol was added to the resulting supernatants in an equal amount, and the mixture was shaken under cooled conditions and then subjected to centrifugal separation to obtain a water layer. To the water layer is added a water-saturated phenol, and the shaking and centrifugal separation were repeated twice. The water layer thus obtained was combined together, and ethyl ether was added. After shaking the mixture, the water layer was collected, with eventual removal of excess ether. Pure ethanol in an amount of four times as much was added to the water layer obtained, and the mixture was left overnight in a cool dark chamber (−25° C.). The precipitate obtained was centrifugally separated and freeze dried to give 1.2 g of a white amorphous powder of TH69E.

EXAMPLE 2

20 g of TH69E and 0.9 g of sodium chloride were dissolved in distilled water for injection to make the total amount to be 100 ml, thereby obtaining an injection composition. This may be injected one or a few times a day, each time in an amount of 1 to 10 ml.

EXAMPLE 3

20 g of TH69E and 80 g of lactose were mixed to obtain a powder composition. This may be administered a few times a day in an amount of 1 to 5 g per day.

EXAMPLE 4

Tablets were prepared, each of which contained 100 mg of TH69E, 100 mg of lactose and 35 mg of starch. 2 to 10 tablets per day may be administered a few times a day.

EXAMPLE 5

Capsules were prepared, each of which contained 200 mg of TH69E, 100 mg of lactose and 3 mg of magnesium stearate. 1 to 5 capsules per day may be administered a few times a day.

Having now fully described this invention, it will be apparent to one of ordinary skill in the art that many changes and modifications can be made thereto without departing from the spirit or scope of the invention set forth herein.

What is claimed is:

1. A substance TH69E having the characteristics:
   (a) elemental analysis: C:24.25%, H: 4.46% and N:6.55%
   (b) molecular weight: about 60,000 ±15,000 (Biogel P-Series Column);
   (c) color: white amorphous powder;
   (d) decomposition point: 80° C. (as determined by a capillary method with use of Silicone Oil WF-30—the color changes to brown);
   (e) ultraviolet absorption spectrum: as shown in FIG. 1 of the drawings;
   (f) infrared absorption spectrum: as shown in FIG. 2 of the drawings;
   (g) pH: 6.7 to 7.1 in an aqueous solution;
   (h) solubility: soluble in water, and insoluble in ethanol, acetone, n-hexane, n-butanol and phenol; and
   (i) color reactions: phenol-sulfuric acid reaction, anthrone reaction, Molisch reaction, orcinol-hydrochloric acid reaction, Ninhydrin reaction being positive, and Elson-Morgan's reaction being negative, prepared by a process, comprising:
   (a) culturing a strain of *Streptococcus faecalis* having the identifying depository number of ATCC-31663 in a nutrient medium until a sufficient amount of the substance is obtained;
   (b) extracting said bacterial strain obtained from the nutrient medium with hot water;
   (c) treating the aqueous solution at least once with water saturated with a phenolic compound; and
   (d) precipitating said TH69E from said treated aqueous solution.

2. A pharmaceutical composition, comprising:
   from 1.5-150 mg. of the TH69E substance of claim 1 per kg of body weight of a host subject in a pharmaceutically acceptable vehicle.

3. The composition of claim 2, wherein said composition is in the form of a capsule.

4. The composition of claim 2, wherein said composition is in the form of a tablet.

5. The composition of claim 2, wherein said composition is in the form of an injectable solution.

6. The composition of claim 2, wherein said composition is in the form of a powder.

* * * * *